United States Patent [19]

Silebi et al.

[11] Patent Number: 5,089,126
[45] Date of Patent: Feb. 18, 1992

[54] METHOD AND APPARATUS FOR CAPILLARY HYDRODYNAMIC FRACTIONATION

[75] Inventors: Cesar A. Silebi, Lower Gwynedd; Jose D. Ramos, Milford, both of Pa.

[73] Assignee: Lehigh University, Bethlehem, Pa.

[21] Appl. No.: 332,021

[22] Filed: Mar. 31, 1989

[51] Int. Cl.$^5$ .............................................. B01D 15/08
[52] U.S. Cl. ............................. 210/198.20; 210/656; 210/659; 422/70; 73/61.1 C; 436/161; 209/1; 209/155; 209/156
[58] Field of Search ............... 422/70; 210/198.2, 635, 210/656, 659; 73/61.1 C; 436/161; 209/1, 2, 155, 156

[56] References Cited

U.S. PATENT DOCUMENTS

| | | | |
|---|---|---|---|
| 3,373,872 | 3/1968 | Hrdina | 210/659 |
| 3,865,717 | 2/1975 | Small | 210/656 |
| 4,066,536 | 1/1978 | Ball et al. | |
| 4,271,697 | 6/1981 | Mowery, Jr. | 210/659 |
| 4,424,127 | 1/1984 | Roeraade | 210/198.2 |
| 4,455,084 | 6/1984 | Webb, Jr. et al. | 210/659 |
| 4,532,043 | 7/1985 | Prud'homme et al. | 210/635 |
| 4,629,566 | 12/1986 | Prud'homme et al. | 210/635 |
| 4,681,678 | 7/1987 | Leaseburge et al. | 210/198.2 |
| 4,950,397 | 8/1990 | Oqueno et al. | 210/659 |

OTHER PUBLICATIONS

"An Analysis of Flow Separation in Hydrodynamic Chromatography of Polymer Latexes", *AIChE Journal*, vol. 24, No. 2, pp. 204–212, Mar. 1978.
"Separation by Flow", DiMarzio et al., 1970.
"Separation of Submicrometer Particles by Capillary Hydrogynamic . . . ", Silebi et al., 4/3/89.

*Primary Examiner*—Stanley S. Silverman
*Assistant Examiner*—Neil M. McCarthy
*Attorney, Agent, or Firm*—Ratner & Prestia

[57] ABSTRACT

This invention provides an apparatus and method for the complete fractionation of submicron particles according to size by capillary hydrodynamic fractionation. This objective is achieved by using small diameter capillaries; introducing a minor fraction of a liquid dispersion of particles to be separated into at least one capillary fraction; passing the minor fraction through the capillary; and, at the exit of the capillary, diluting the minor fraction with the same liquid as is carrying the fractionated sample. These modifications in the flow patterns are essential to the use of capillaries with diameters smaller than 60 microns. This invention is especially adapted for rapid analytical separation of not only rigid colloidal particles but also of soft latexes.

9 Claims, 8 Drawing Sheets

METHOD AND APPARATUS FOR CAPILLARY HYDRODYNAMIC FRACTIONATION

FIELD OF THE INVENTION

This invention relates generally to the separation of submicron-sized particles by hydrodynamic fractionation.

DESCRIPTION OF RELATED ART

Separation by flow was first proposed on theoretical grounds by DiMarzio and Guttman (*Polymer Letters* 7 267 (1969)). According to their analysis, separation by flow according to particle size is due to two factors: (i) the radial velocity profile developed by a fluid moving through a capillary tube allowing the particles to move at different speeds and (ii) the inability of larger particles to approach the capillary wall as closely as smaller particles, which causes the larger particles to sample fluid streamlines of higher velocity, moving on the average at speeds greater than the average eluant velocity.

Separation of micron sized particles by flow through tubes has been described by Noel et al. (*J. Chromatography* 166, 373 (1978)) and Mullins and Orr (*Int. J. Multiphase Flow* 5, 79 (1979)) using long capillary tubes (50 to 200 meters in length), with inner diameters in the range from 250 to 500 microns, to fractionate particles with diameters greater than one micron. Although these investigators achieved separations between submicron particles and particles larger than a micron, they were not able to fractionate mixtures of submicron particles. Brough and coworkers (*J. Chromatography*, 208, 175 (1981)) used smaller capillary tubes (150 microns in diameter) in an effort to expand the size range of the fractionation. Although Brough and coworkers were able to detect differences in elution times between submicron particles, their resolution was not sufficient to resolve bimodal mixtures of submicron particles. de Jaeger et al. (*P. Charact.* 3, 187, (1986)) improved the resolution of the separation by using a slightly smaller diameter capillary (100 microns) in conjunction with a block copolymer, dissolved in the eluant stream, that absorbs on the capillary wall and the particle surface. These investigators were able to detect the presence of submicron particles in polydisperse samples containing mixtures of different monodisperse standards.

SUMMARY OF THE INVENTION

This invention provides an apparatus and method for the complete fractionation of submicron particles according to size by capillary hydrodynamic fractionation. This objective is achieved by using small diameter capillaries; introducing a minor fraction of a liquid dispersion of particles to be separated into at least one capillary; passing the minor fraction through the capillary; and, at the exit of the capillary, diluting the minor fraction with the additional solvent. These modifications in the flow patterns are essential to the use of capillaries with diameters smaller than 60 microns. This invention is especially adapted for rapid analytical separation of not only rigid colloidal particles but also of soft latexes, ultrahigh molecular weight biopolymers, and macromolecules.

DETAILED DESCRIPTION OF THE INVENTION

As used herein, the term "monodisperse" means that the dispersed particles are all of essentially one size and the term "polydisperse" means that the dispersed particles include a range of sizes.

In accordance with the invention there is provided an apparatus and method for the separation of a polydisperse dispersion of particles in a fluid by size which comprises passing the dispersion of particles through a capillary tube whose diameter is several times larger than the particles to be separated and eluting the capillary tube with a further portion of the dispersing medium whereby the larger particles of the dispersion elute from the capillary first and successively smaller particles elute subsequently.

Figure 1:
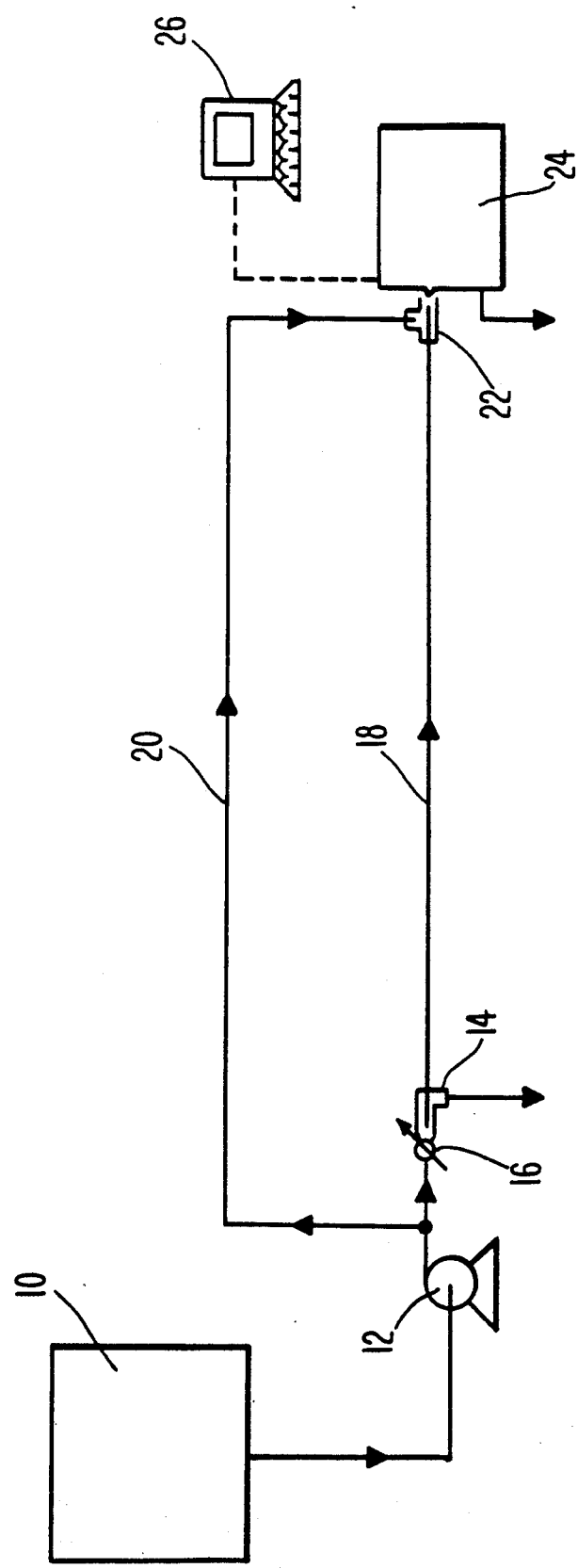
FIG. 1 is a schematic of the capillary hydrodynamic fractionator of this invention.

A schematic diagram of a typical fractionation system employing the principles of this invention is shown in FIG. 1. Reservoir 10 supplies solvent, optionally with a surfactant, via pump 12 to stream splitter 14. The sample of particles dispersed in liquid is introduced via injection port 16 situated upstream from stream splitter 14. A major portion of the stream is discharged to waste; a minor fraction of the stream passes through one or more capillary hydrodynamic fractionation (CHDF) tubes 18 where the particles are separated by velocity profile. After passage through CHDF tubes 18, the separated dispersion is diluted with additional solvent, or make-up fluid, pumped via tube 20, at stream merger 22. The diluted, separated sample is then passed to a suitable analyzer, such as UV detector 24, optionally interfaced to computer 26.

In one embodiment, a pump, such as a Laboratory Data Control Model 1396-57 dual pump with a pulse dampener was used to pump the eluant through the capillary tube. This pump is capable of a maximum pressure of 5000 psi and the flow rate can be adjusted from 580 ml/h down to 29 ml/h. The sample is injected into the eluant stream, without interrupting flow to the capillary, through a Rheodyne Model 7413 sample injection valve with selectable sample loops of 0.5, 1, and 5 l.

The open capillary tubes used were of fused silica and were supplied by Polymicro Technologies, in lengths of 1 to 50 m, with diameters of 4, 7, 14, 34, and 60 microns.

Since the problems caused by dead volume in the injection and detection systems are considerably more severe with these narrow capillaries than with larger inner diameter capillaries, the flow around both injection and detection systems has been modified. In order to minimize dead volume effects, the eluting solution was split into two streams after passing through the injection valve, while at the exit of the capillary more eluant was added to the stream entering the detector cell. The sample splitting and make-up ratios used ranged from 1:100 to $1:10^7$ and above depending on the diameter of the capillaries and flow rate through the microcapillary. For every combination of capillary and flow rate, the splitting and make-up ratios that give the least peak spreading should be used.

A minipump was used to pump the make-up eluant, which is mixed with the fluid exiting from the capillary through the detector cell. The detector used was a Laboratory Data Control SM 4000 Programmable UV-Light Detector fitted with a 14-1 flow cell. The colloid and marker species were detected in the effluent by monitoring turbidity at 220 nm (but other wavelengths can be used). The output from the detector was monitored both on a strip chart recorder and also digitally with a disk drive interfaced to the detector through an Analog Devices DAS1155 A/D converter and a Frequency Devices four-pole Bessel active filter. Digital data analysis was carried out on a microcomputer, and the processed results were output to a dot matrix printer.

The eluant is generally the same solvent as that in which the sample to be fractionated is dispersed. Preferably, the eluant contains one or more surfactants, in a concentration of from 0.0001M to 0.1M such as sodium lauryl sulfate or a polyoxyalkylene glycol. Most preferably, the surfactant is a mixture of sodium lauryl sulfate and polyoxyethylene lauryl alcohol.

A wide variety of capillary tubes may be employed in the present invention. Generally, the shape of the capillary is not critical. However, most conveniently employed is a cylindrical capillary tube. The capillary tube desirably has a surface which is generally inert to the dispersing or suspending medium employed; that is, it is insoluble in the dispersing medium, and if coated by solutions in the dispersing medium, it will not absorb particles onto the capillary wall. It is essential and critical in the practice of the present invention that the particles being separated do not adhere to the inner wall of the capillary tube and form multiparticle layers thereon. The capillary tubes may be constructed of a wide variety of materials such as, for example, fused silica, glass, plastics and metal. Eminently satisfactory for many applications are fused silica glass or plastic tubes from about 3 to 30 microns inside diameter. Advantageously, the process of the present invention is used for separating polydisperse synthetic latex particles which range in size from about 100 Angstroms to as large as 1 to 5 microns, and is preferably employed in separating polydisperse latex particles having a size range of from 100 Angstroms to 2 microns and most advantageously having a size range of 0.05 to 0.5 microns. Usually it is desired that the inside diameter of the capillary tube be from 5 to 50 times the diameter of the largest latex particles to be separated. Typically, the capillary tube has a length varying from 10 centimeters to 50 or 100 meters or more, depending upon the degree of separation desired. Typical operating pressures for capillaries 7 microns in diameter and 3 meters in length generally are from about 300 to 6000 pounds per square inch. For most applications, particularly for small scale laboratory operations or for analytical procedures, it is usually desirable to employ a capillary tube of small diameter and substantial length, such as 5 microns in diameter and 10 meters in length. Such capillaries, if formed with flexible silica tubing or synthetic plastic tubing or flexible metal tubing, may be conveniently coiled to occupy a minimum of space. More than one capillary tube, connected in series or in parallel or both, may be employed.

EXAMPLE 1

Figure 2:
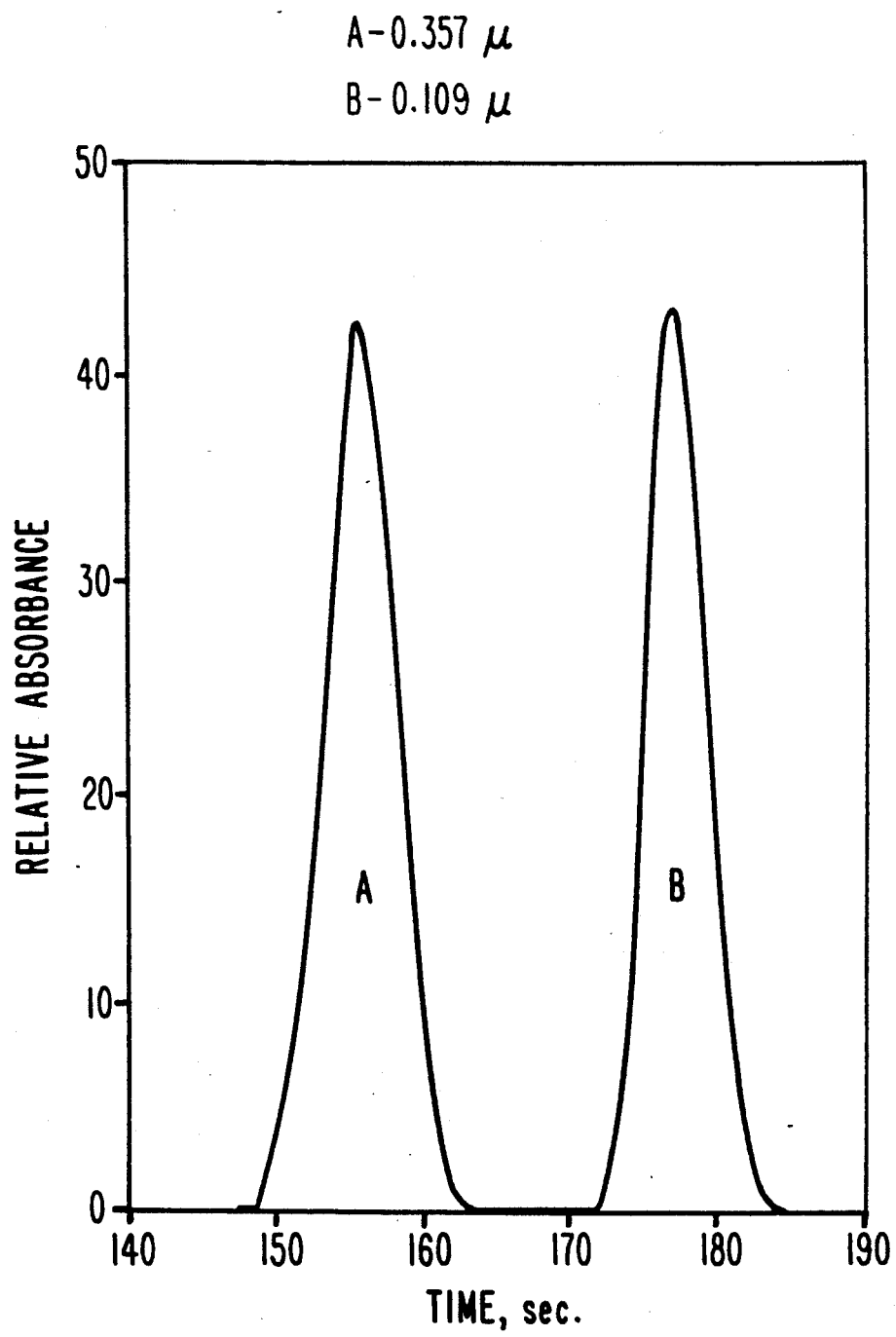
FIGS. 2-8 are representative spectrometer tracings of separated dispersions.

A mixture was prepared of two monodisperse polystyrene latexes having particle diameters of 0.357 micron and 0.109 micron respectively. The polydisperse latex so formed was diluted to 3 weight percent with deionized water containing $10^{-3}$ molar sodium lauryl sulfate. The capillary tube has an average diameter of 4 microns. Deionized water containing the surfactant was pumped through the system at a rate of 1 milliliter per minute, of which $1.13 \times 10^{-7}$ l/min pass through the capillary. 0.005 milliliters of the latex mixture was introduced through the sample injection valve and the turbidity of the effluent recorded on a strip chart recorder. A distinct separation of the 0.109 micron and 0.357 micron particles was observed after a period of about 3 minutes. The plot of absorbency versus time of FIG. 2 indicates the relatively sharp separation of the larger and smaller particles.

EXAMPLE 2

Figure 3:
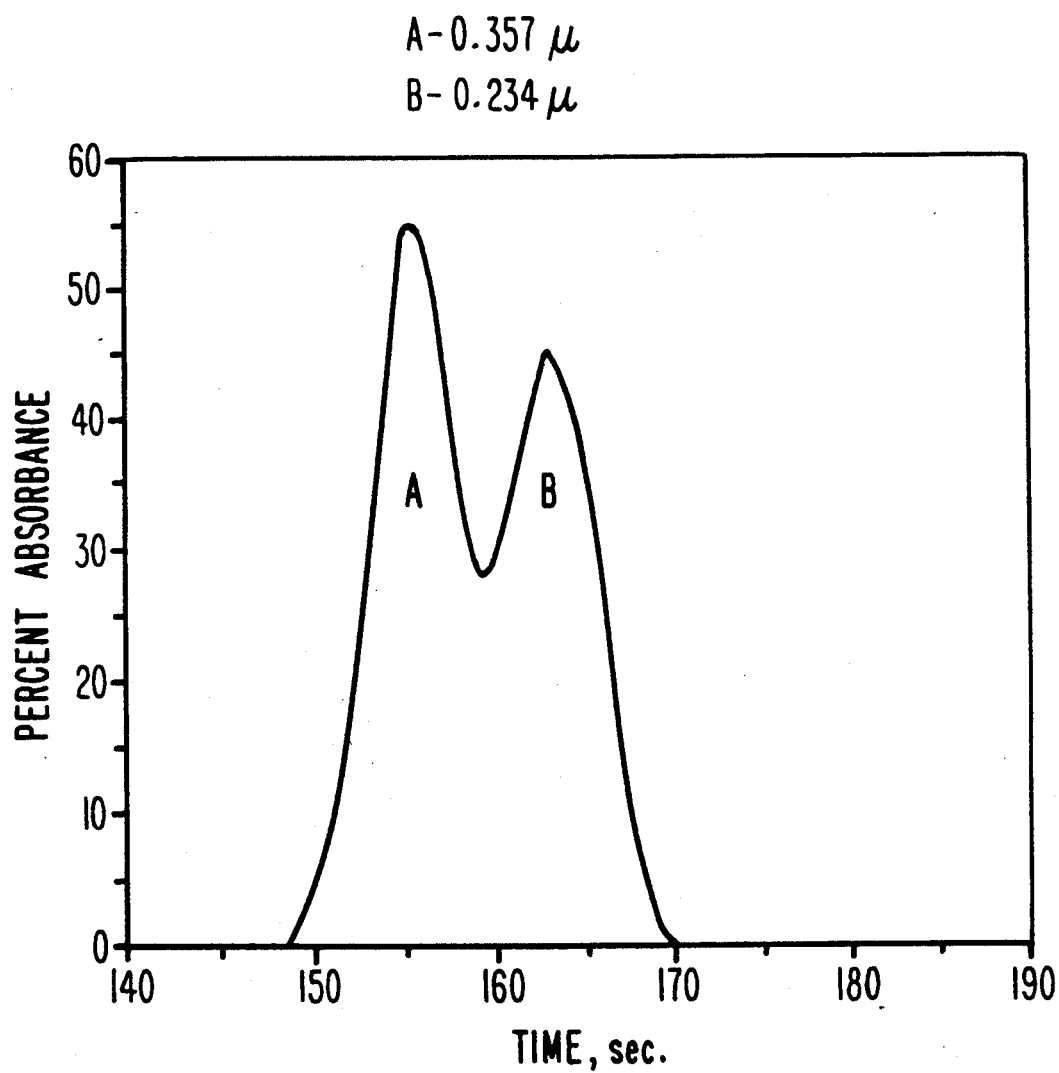

The procedure of Example 1 was repeated with a mixture of 0.234 micron and 0.357 micron monodisperse latexes. The plot, as shown in FIG. 3, consists of a bifurcated peak, with the peak of the larger size particles appearing 155 seconds after sample injection and the peak of the smaller particles 163 seconds after injection.

EXAMPLE 3

Figure 4:
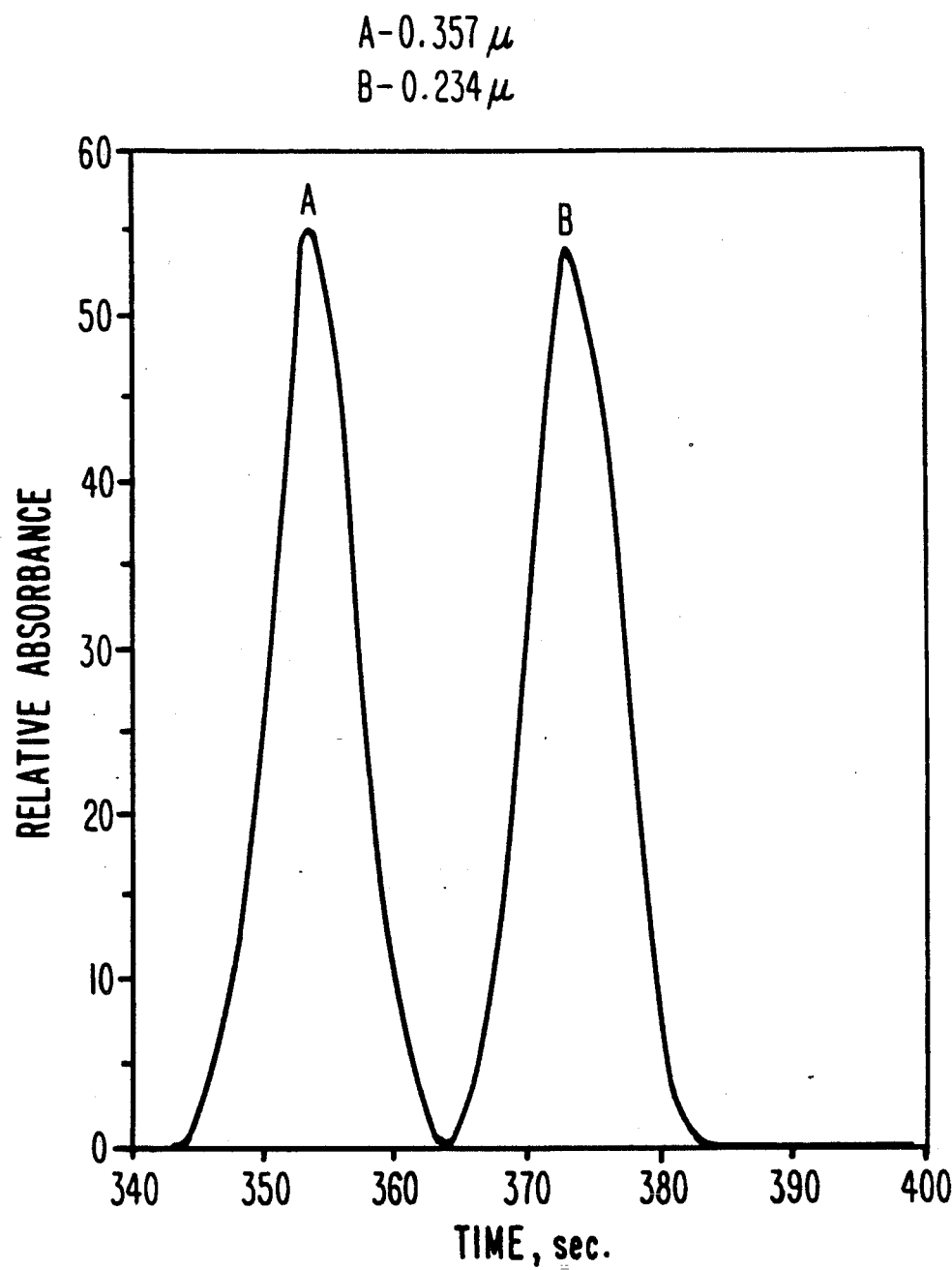

The procedure of Example 2 was repeated with the exception that the average velocity of the eluant through the capillary tube was reduced to 0.67633 $10^{-7}$ l/min. A complete separation of the two latexes was obtained as set forth in FIG. 4.

EXAMPLE 4

Figure 5:
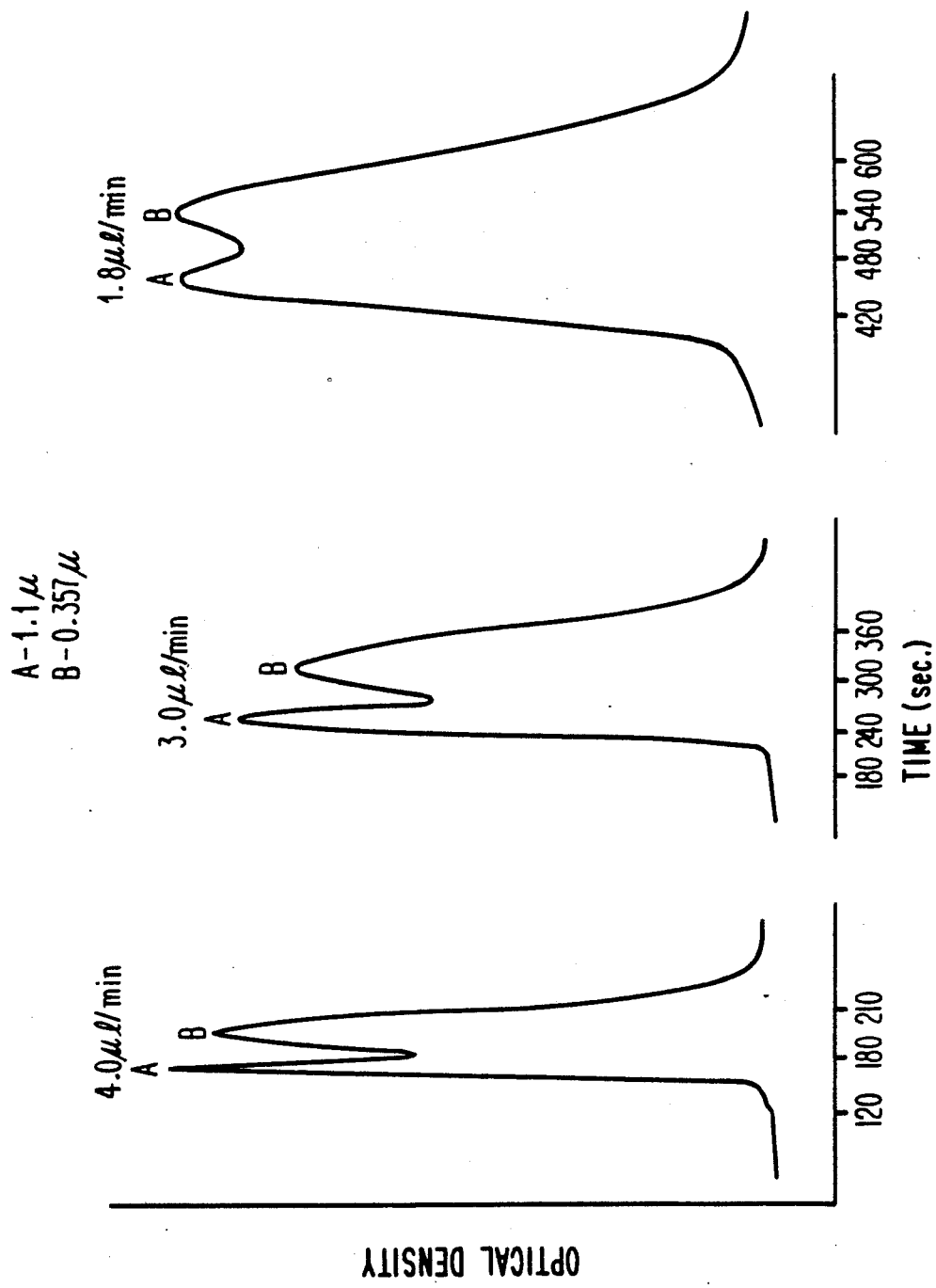

The procedure of Example 1 was repeated with a mixture of particles with diameters of 0.357 and 1.1 microns injected into the system, connected to a capillary tube of diameter 34 microns and length 20 meters. The flow rates through the injection valve were 0.41, 0.29, and 0.18 ml/min while the corresponding flow rates through the capillaries were 4, 3 and 1.8 µl/min respectively. A partial separation of the two latexes was obtained as indicated in FIG. 5, which is a representation of the trace obtained from the recording of the light scattering detector, for different eluant average velocities. Contrary to what was observed with mixtures of submicron particles, illustrated in Examples 2 and 3, in the case of samples containing particles with diameter greater than 0.5 microns, the efficiency of the separation decreases with increasing eluant velocity (shorter elution time).

EXAMPLE 3

The procedure of Example 2 was repeated with the exception that the average velocity of the eluant through the capillary tube was reduced to $0.67 \times 10^{-7}$ l/min. A complete separation of the two latexes was obtained as set forth in FIG. 4.

EXAMPLE 4

The procedure of Example 1 was repeated with a mixture of particles with diameters of 0.357 and 1.1 microns injected into the system, connected to a capillary tube of diameter 34 microns and length 20 meters. The flow rates through the injection valve were 0.41, 0.29, and 0.18 ml/min while the corresponding flow rates through the capillaries were 4, 3 and 1.8 µl/min respectively. A partial separation of the two latexes was obtained as indicated in FIG. 5, which is a representation of the trace obtained from the recording of the light scattering detector, for different eluant average velocities. Contrary to what was observed with mixtures of submicron particles, illustrated in Examples 2 and 3, in the case of samples containing particles with diameter greater than 0.5 microns, the efficiency of the separation decreases with increasing eluant velocity (shorter elution time).

EXAMPLE 5

Figure 6:
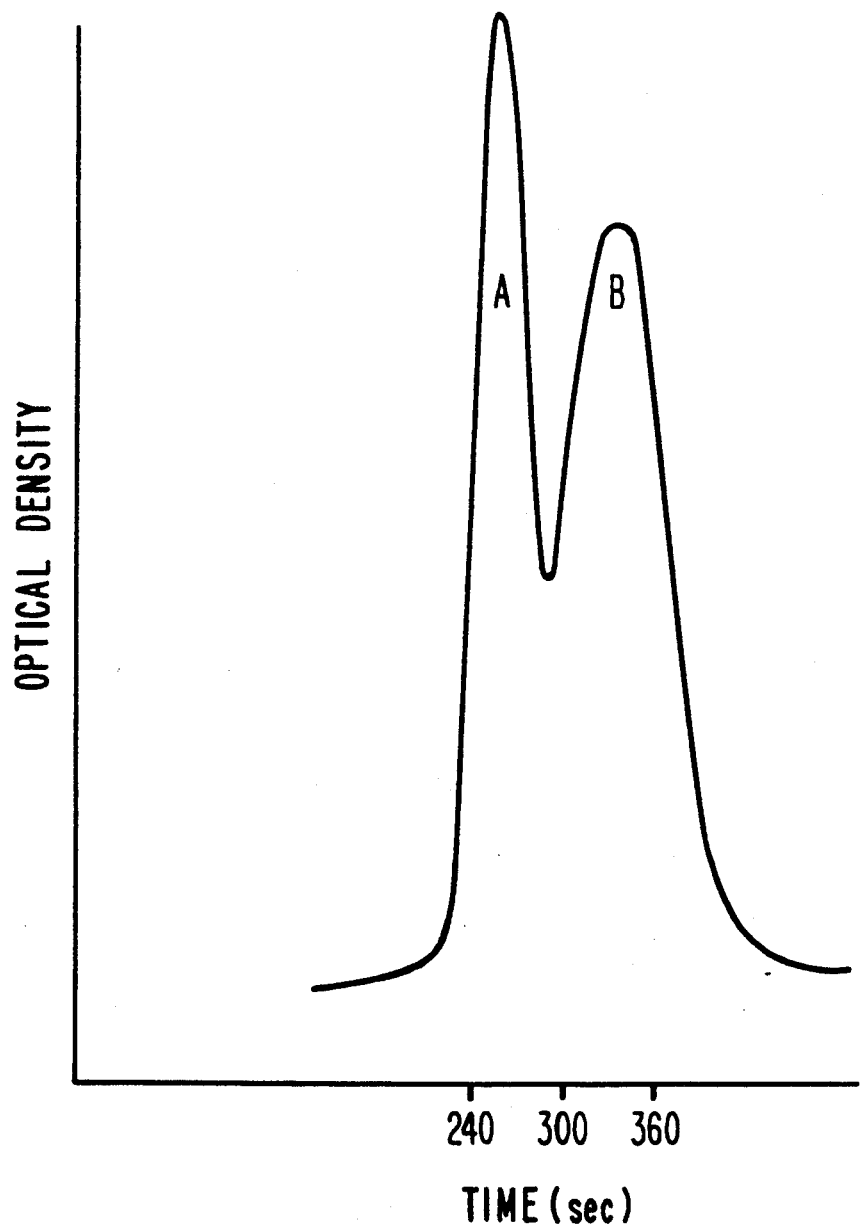

A mixture was prepared of polystyrene latex particles having diameters of 0.357 micron and 1.1 micron and injected into the system of Example 4. The positive displacement pump delivered 1 milliliter per minute of an aqueous solution of a non-ionic surface active agent sold under the trade designation of Pluronic F-108 (BASF), in a concentration of 0.15 gram per liter to the capillary. The flow rate through the capillary tube was 29 μl/min. Good separation of the latex particles was obtained, as is indicated in FIG. 6.

EXAMPLE 6

Figure 7:
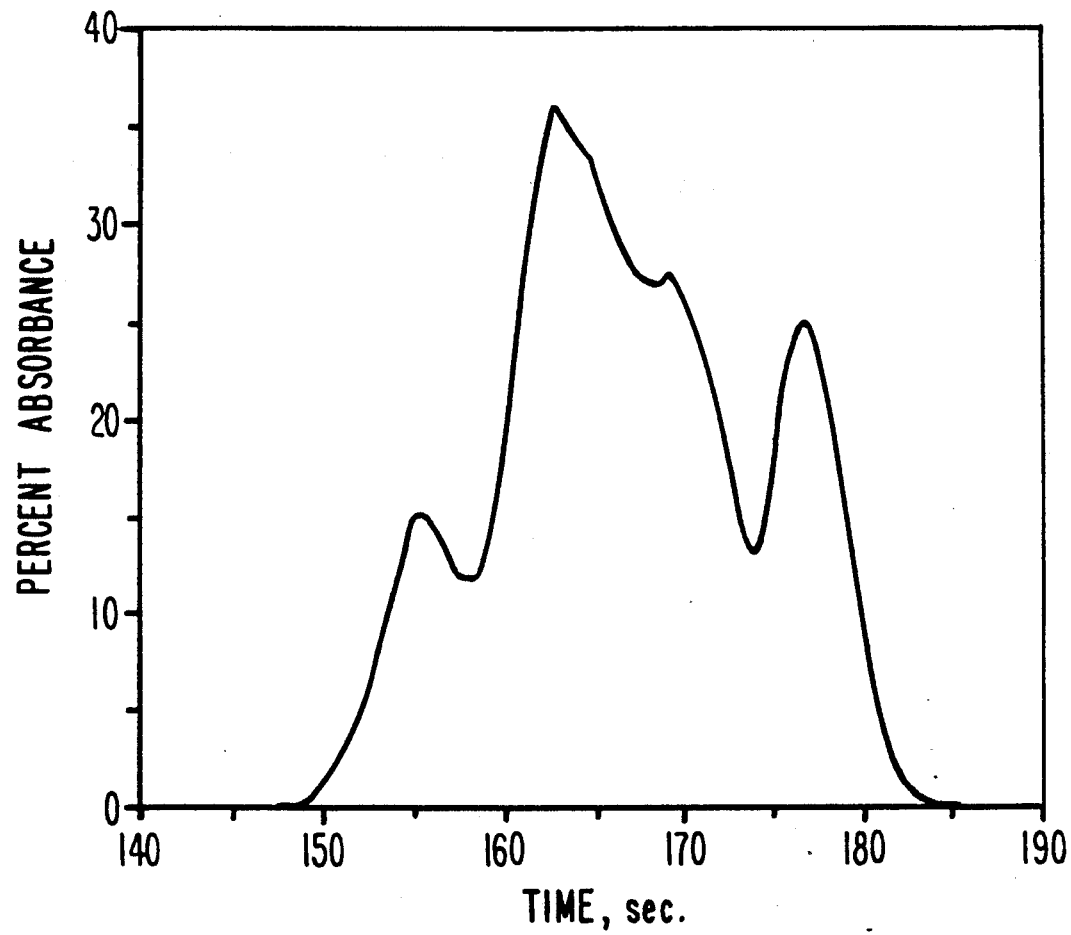

When the procedure of Example 1 was repeated employing a polydisperse latex, a curve was obtained which is characteristic of the particle size distribution. FIG. 7 illustrates the fractionation obtained with a mixture of particles of 0.109, 0.176, 0.234, and 0.357 microns in diameter.

EXAMPLE 7

Figure 8:
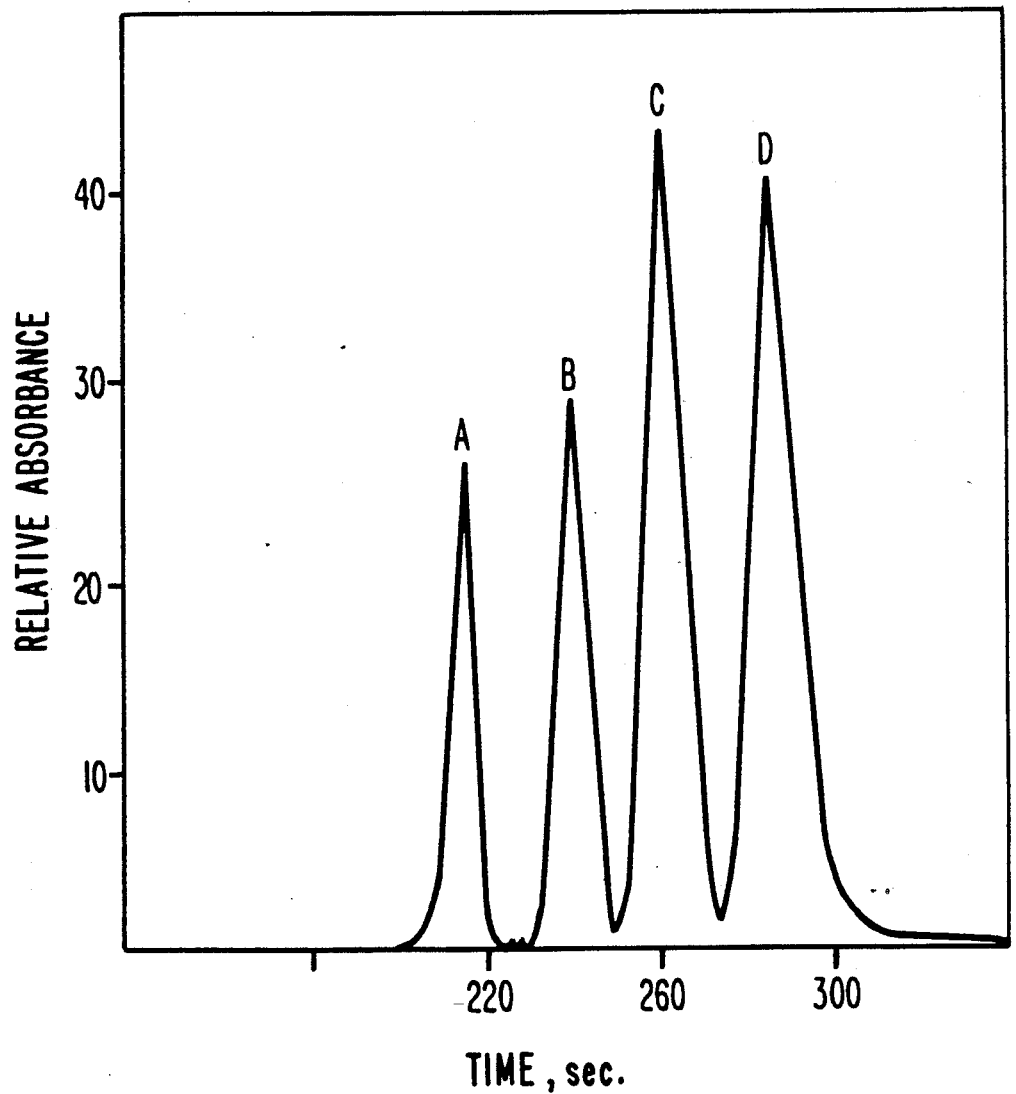

An aqueous solution of $10^{-4}$ molar sodium lauryl sulfate and 0.1% by weight of polyoxyethylene lauryl alcohol was pumped through the system at a rate of 1.3 ml/min. The capillary tube used had an inside diameter of 7.0 microns and a length of 5 m. Flow through the capillary was at a rate of $2.5 \times 10^{-5}$ ml/min. A mixture of polystyrene latex particles having diameters of 0.109, 0.176, 0.234 and 0.357 microns was injected into the flowing aqueous solution of sodium lauryl sulfate and polyoxyethylene lauryl alcohol. A complete separation of the four latexes was obtained as set forth in FIG. 8. In other experiments, larger particles were better separated with a smaller concentration of polyoxyethylene.

What is claimed is:

1. An apparatus for separating particles by size comprising:
   a) means for forming a liquid dispersion of said particles to be separated;
   b) means for splitting said liquid dispersion into major and minor fractions;
   c) means for introducing said minor fraction of the liquid dispersion of particles to be separated into and through at least one capillary tube to produce a distribution of particles of differing size exiting said capillary tube at different times after said introduction;
   d) means for introducing the separated dispersion into a liquid diluent stream as said separated dispersion exits said capillary tube to facilitate collection and measurement thereof by maintaining said distribution of particles;
   e) means for collecting the diluted, separated liquid dispersion and measuring the particle size distribution thereof.

2. An apparatus of claim 1 in which the introducing means comprises an injection port and said splitting means comprises a flow splitter for dividing the liquid dispersion into major and minor fractions.

3. An apparatus of claim 1 in which the means for introducing the separated dispersion into the liquid diluent stream comprises a stream major to combine the separated liquid dispersion with additional liquid.

4. An apparatus for separating particles dispersed in a fluid by size comprising,
   (a) a reservoir containing an eluant;
   b) an array of tubing through which the eluant is circulated connected to the reservoir;
   c) an injection port for introducing a sample of fluid into the eluant in the tubing,
   d) a pump for pumping the sample and the eluant through the tubing;
   e) means for splitting the sample into a major portion and a minor portion;
   f) at least one capillary tube connected to the means for splitting the sample for producing from said minor portion a distribution of particles of differing size exiting said capillary tubes at different times;
   g) means for combining the distribution of particles exiting from the capillary tube with additional eluant for maintaining said distribution of particles; and
   h) means for measuring the particles size distribution of the distribution of particles.

5. An apparatus of claim 4 in which the means for splitting the sample is adapted to provide a ratio of minor portion to major portion of from about 1:100 to about $1:10^7$.

6. An apparatus of claim 1 in which at least one capillary tube has a diameter of from about 4 microns to about 60 microns.

7. An apparatus of claim 1 having at least two capillary tubes connected in series.

8. An apparatus of claim 1 having at least two capillary tubes connected in parallel.

9. An apparatus of claim 4 in which the means for splitting the sample is a flow splitter, the means for combining the distribution of particles exiting from the capillary tube with the eluant is a three-way connector, and the means for measuring the particle size distribution is a UV-visible spectrophotometer.

* * * * *

UNITED STATES PATENT AND TRADEMARK OFFICE
CERTIFICATE OF CORRECTION

PATENT NO. : 5,089,126
DATED : Feb. 18, 1992
INVENTOR(S) : Cesar A. Silebi et al.

It is certified that error appears in the above—identified patent and that said Letters Patent is hereby corrected as shown below:

On front cover sheet, following "(75) Inventors:"
"Jose D. Ramos" should be corrected to "Jose Dos Ramos."

Column 4, lines 26 through 50, delete the <u>first</u> printing of Examples 3 and 4.

Column 6, line 3, after the second occurrence of "stream" delete "major" and insert --merger--.

Signed and Sealed this

Tenth Day of August, 1993

Attest:

MICHAEL K. KIRK

*Attesting Officer*     *Acting Commissioner of Patents and Trademarks*